US00PP24997P2

(12) United States Plant Patent
Hartman

(10) Patent No.: US PP24,997 P2
(45) Date of Patent: Oct. 21, 2014

(54) ***CALADIUM* PLANT NAMED 'FIREWORKS'**

(50) Latin Name: *Caladium×hortulanum*
Varietal Denomination: Fireworks

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 36 days.

(21) Appl. No.: 13/815,203

(22) Filed: Feb. 8, 2013

(51) Int. Cl.
*A01H 5/00* (2006.01)

(52) U.S. Cl.
USPC ..... Plt./373

(58) Field of Classification Search
USPC ..... Plt./373
See application file for complete search history.

*Primary Examiner* — Annette Para
(74) *Attorney, Agent, or Firm* — C. A. Whealy

(57) ABSTRACT

A new and distinct cultivar of *Caladium* plant named 'Fireworks', characterized by its upright plant habit; intermediate to tall plant size; uniform plant habit; vigorous and dense growth habit; glossy to shiny fancy-type leaves with medium to dark green-colored background and border centrally marked with coalescing dark red-colored spots and blotches; with development, spots and blotches almost cover the entire leaf surface; spots and blotches surrounded with white-colored borders; dark purple-colored leaf venation; and good landscape performance.

4 Drawing Sheets

Botanical designation: *Caladium×hortulanum.*
Cultivar denomination: 'FIREWORKS'.

BACKGROUND OF THE INVENTION

The present invention relates to a new and distinct cultivar of *Caladium* plant, botanically known as *Caladium×hortulanum*, commercially referred to as a fancy leaf-type *Caladium* and hereinafter referred to by the name 'Fireworks'.

The objective of the Inventor's breeding program is to create new *Caladium* plants that have uniform plant habit, exceptional container and garden performance and attractive foliage coloration.

The new *Caladium* plant is a naturally-occurring whole plant mutation of *Caladium×hortulanum* 'Fire Chief', not patented. The new *Caladium* plant was discovered and selected by the Inventor as a single plant from within a population of plants of 'Fire Chief' in a controlled outdoor nursery environment in Zolfo Springs, Fla. on Sep. 15, 2008.

Asexual reproduction of the new *Caladium* plant by 'chipping' the tubers (cutting the tuber into segments with each segment containing an axillary bud and tuber cortical tissue) in a controlled outdoor nursery environment in Lake Placid, Fla. since Apr. 15, 2009 has shown that the unique features of this new *Caladium* plant are stable and reproduced true to type in successive generations of asexual reproduction.

SUMMARY OF THE INVENTION

Plants of the new *Caladium* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Fireworks'. These characteristics in combination distinguish 'Fireworks' as a new and distinct *Caladium* plant:

1. Upright plant habit; intermediate to tall plant size.
2. Uniform plant habit.
3. Vigorous and dense growth habit.
4. Glossy to shiny fancy-type leaves with medium to dark green-colored background and border centrally marked with coalescing dark red-colored spots and blotches; with development, spots and blotches almost cover the entire leaf surface; spots and blotches surrounded with white-colored borders; venation, dark purple in color.
5. Good landscape performance.

Plants of the new *Caladium* differ primarily from plants of the parent, 'Fire Chief', in leaf color as plants of 'Fire Chief' have fancy-type leaves with medium green-colored background and border centrally marked with coalescing rose pink-colored spots and blotches that with development cover less than half of the entire leaf surface and with green-colored venation. In addition, plants of the new *Caladium* and 'Fire Chief' differ in leaf petiole coloration.

Plants of the new *Caladium* can be compared to plants of *Caladium* 'Frieda Hemple', not patented. In side-by-side comparisons plants of the new *Caladium* differed primarily from plants of 'Frieda Hemple' in the following characteristics:

1. Potted plants of the new *Caladium* finished about one to two weeks later than potted plants of 'Frieda Hemple'.
2. Plants of the new *Caladium* were not as freely branching than plants of 'Frieda Hemple'.
3. Leaves of plants of the new *Caladium* were glossier than leaves of plants of 'Frieda Hemple'.
4. Plants of the new *Caladium* and 'Frieda Hemple' differed in leaf coloration as leaves of plants of 'Frieda Hemple' had medium green-colored leaves with broad red-colored centers.

Plants of the new *Caladium* can be compared to plants of *Caladium* 'Postman Joyner', not patented. In side-by-side comparisons plants of the new *Caladium* differed primarily from plants of 'Postman Joyner' in the following characteristics:

1. Plants of the new *Caladium* were taller and more vigorous than plants of 'Postman Joyner'.
2. Potted plants of the new *Caladium* finished about one to two weeks later than potted plants of 'Postman Joyner'.
3. Plants of the new *Caladium* were not as freely branching than plants of 'Postman Joyner'.
4. Leaves of plants of the new *Caladium* were glossier than leaves of plants of 'Postman Joyner'.
5. Plants of the new *Caladium* and 'Postman Joyner' differed in leaf coloration as leaves of plants of 'Postman Joyner' had dark green-colored leaves with red-colored centers and dark red-colored spots and blotches.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet is a side perspective view of a typical plant of 'Fireworks' grown in a 15-cm container in a shadehouse, and the plant has had its tuber de-eyed.

The photograph at the top of the second sheet is a side perspective view of typical plants of 'Fireworks' grown in an outdoor nursery.

The photograph at the bottom of the second sheet is a close-up view of a typical freshly-harvested tuber and roots of 'Fireworks'.

The photograph at the top of the third sheet is a comparison view of typical plants of 'Fireworks' grown in 15-cm containers, the plant on the left has not had its tuber de-eyed and the plant on the right has had its tuber de-eyed prior to planting.

The photograph at the bottom of the third sheet is a close-up view of a typical inflorescence of 'Fireworks'.

The photograph at the top of the fourth sheet is a comparison view of typical potted plants of 'Fireworks' (left) and the parent, 'Fire Chief' (right).

The photograph at the bottom of the fourth sheet is a comparison view of typical potted plants of 'Frieda Hemple' (left), 'Fireworks' (center) and 'Postman Joyner' (right).

DETAILED BOTANICAL DESCRIPTION

The aforementioned photographs and following observations and measurements describe plants grown during the winter in 15-cm containers in Avon Park, Fla. in a polypropylene-covered shadehouse (30% light reduction) and plants grown during the spring and summer in ground beds in an outdoor nursery in Crewsville, Fla. The plants were grown under cultural practices typical of commercial shadehouse and outdoor nursery *Caladium* production. During the production of the plants, day temperatures ranged from about 29° C. to 33° C. (shadehouse) or 29° C. to 35° C. (outdoor nursery), night temperatures ranged from about 22° C. to 25° C. (shadehouse) or 22° C. to 26° C. (outdoor nursery) and light levels were about 8,000 foot-candles (shadehouse) or 10,000 to 12,000 foot-candles (outdoor nursery). Plants grown in the shadehouse were eight weeks old when the photographs and the detailed description were taken. Plants grown in the outdoor nursery were six months old when the photographs and the detailed description were taken. In the following description, color references are made to The Royal Horticultural Society Colour Chart, 2001 Edition, except where general terms of ordinary dictionary significance are used.

Botanical classification: *Caladium×hortulanum* 'Fireworks'.

Parentage: Naturally-occurring whole plant mutation of *Caladium×hortulanum* 'Fire Chief', not patented.

Propagation:

*Type*.—By "chipping" the tubers.

*Time to initiate roots, summer*.—About seven to ten days at 32° C.

*Time to initiate roots, winter*.—About two to three weeks at 24° C.

*Tuber description* (*outdoor nursery-grown plants*).—Appearance: Multi-segmented and somewhat flattened; individual segments ovate to elliptic in shape. Height: About 3.5 cm. Diameter: About 5.1 cm. Segment height: About 2.5 cm. Segment diameter: About 2.5 cm. Texture: Thick, starchy; somewhat brittle. Color: Epidermis, freshly-harvested: Close to 199A to 199C and 200B to 200C. Epidermis, dried: Close to 200A to 200B. Cortical tissue: Close to 1D. Axillary buds: Close to 36D. Root description: Thick, fleshy contractile roots; color, close to 155C. Rooting habit: Few lateral branches; moderately dense.

Plant description:

*Plant type*.—Herbaceous perennial; suitable as a potted plant in containers 15-cm to 25-cm and suitable as a landscape plant in shaded areas.

*Plant and growth habit*.—Upright plant habit; intermediate to tall plant size; inverted triangle; vigorous and dense growth habit; rapid growth rate, potted plants in finished or saleable form in about eight to nine weeks after planting tubers; leaf petioles and leaves arise from one or more growing points on tubers; petioles mostly upright and arching outwardly with development.

*Plant height, from soil level to top of foliar plane, shadehouse-grown potted plants*.—About 30 cm to 40 cm.

*Plant height, from soil level to top of inflorescences, field-grown plants*.—About 48 cm.

*Plant diameter or spread, shadehouse-grown potted plants*.—About 43 cm to 50 cm.

*Number of clumps per plant, shadehouse-grown potted plants*.—About two to three from de-eyed tubers.

*Cataphylls, shadehouse-grown potted plants*.—Length: About 5.5 cm to 12 cm. Width: About 1.5 cm to 1.8 cm. Shape: Wedge-like. Apex: Acute. Base: Sheathing the stem. Color, outer surface: Close to N170D tinged with close to 148C and streaked, stippled and tessellated with close to 200B tinged with close to 147B; with development, color becoming closer to N199B stained with close to 187A to 187B. Color, inner surface: Close to 155C.

Foliage description:

*Arrangement and type*.—Alternate; simple; fancy-type.

*Length, shadehouse-grown potted plants*.—About 20.5 cm to 31 cm.

*Width, shadehouse-grown potted plants, flattened*.—About 13.5 cm to 21 cm.

*Shape*.—Broadly ovate to cordate.

*Apex*.—Acute to acuminate.

*Base*.—Sagittate, peltate.

*Margin*.—Entire; mostly flat with some broad undulations; with development becoming more undulate.

*Texture, upper surface*.—Smooth, glabrous; somewhat rugose.

*Texture, lower surface*.—Smooth, glabrous; somewhat rugose.

*Luster, developing leaves, upper surface*.—Somewhat glossy to shiny.

*Luster, fully expanded leaves, upper surface*.—Glossy to shiny.

*Luster, developing and fully expanded leaves, lower surface*.—Glaucous, dull.

*Venation pattern*.—Pinnate.

*Color, shadehouse-grown potted plants*.—Developing leaves, upper surface: Background color: Close to 147A tinged with close to 146A. Central spots and blotches: Close to 53C tinged with close to 184D; edges or borders of spots, close to 155C. Margin: Close to 187A. Basal notch: Close to 53A. Venation between basal notch and petiole attachment: Close to 187A. Midrib and primary venation: Close to 187B flecked with close to N189A. Developing leaves, lower surface: Background color: Close to 147B tinged with close to 148B. Central spots and blotches: Close to 187C and 187D; edges or borders of spots, close to 49D. Margin: Close to 187B. Basal notch: Close to 187A. Venation between basal notch and petiole attachment: Close to 187A. Midrib: Close to 184A. Primary venation: Close to 148A surrounded with flecks and speckles, close to 184A. Fully expanded leaves, upper surface: Background color: Close to 147A tinged with close to 146A. Central spots and blotches: Close to 53B to 53C; edges or borders of spots, close to 155C; some spots, close to 147B and/or 155A. Margin: Close to 187A. Basal notch: Darker than 53A. Venation between basal notch and petiole attachment: Close to 187A. Midrib: Close to 187A to 187B. Primary venation: Close to 187A to 187B flecked with close to N189A. Fully expanded leaves, lower surface: Background color: Close to 191A. Central spots and blotches: Close to 185C and 47B; edges or borders of spots, close to 49C to 49D. Margin: Close to 187A to 187B. Basal notch: Close to 53A. Venation between basal notch and petiole attachment: Close to 187A. Midrib: Close to 184A to 184B. Primary venation: Close to 148A flecked with 184A and surrounded with flecks and speckles, close to 184A.

*Petiole*.—Aspect: Mostly upright, slightly outwardly arching with development; flexible. Length, shadehouse-grown potted plants: About 26 cm to 31 cm. Diameter, distal, shadehouse-grown potted plants: About 4 mm to 6.5 mm. Diameter, proximal, shadehouse-grown potted plants: About 8 mm to 11 mm. Color, shadehouse-grown potted plants: Just below leaf and petiole junction, close to 184A; overall, close to 182B and streaked, stippled and tessellated with close to 200B tinged with close to 147A or almost black, close to 200A to 200B with variably streaked with close to 182B. Wing length, shadehouse-grown potted plants: About 5.5 cm to 7 cm. Wing diameter, shadehouse-grown potted plants: About 6 mm to 10 mm. Wing color, shadehouse-grown potted plants, outer surface: Close to N170D tinged with close to 148C and streaked, stippled and tessellated with close to 200B tinged with close to 147B; or close to 200A to 200B variably streaked with close to N170D tinged with close to 147B. Wing color, shadehouse-grown potted plants, inner surface: Close to 196C to 196, outer surface colors and patterns visible.

Inflorescence description: Inflorescences observed on six month-old field-grown plants.

*Inflorescence arrangement*.—Upright hooded spathes surrounding a columnar spadix borne on a tall upright scape; spadix with sessile, simple female and male flowers separated into two zones; female flowers develop on the lower one-third of the spadix; male flowers develop on the upper two-thirds of the spadix; sterile flowers develop at junction of female and male flower zones; near this junction, the spathe constricts and surrounds and encloses the female flowers; spathe open and cupped around male flowers.

*Fragrance*.—Night and morning fragrant; moderate jasmine-like fragrance with camphor-like notes.

*Natural flowering season and flower longevity*.—Plants of the new *Caladium* typically flower during the spring or summer in central Florida; flowers develop about six months after growth commences; inflorescences last about three days before fading; inflorescences persistent.

*Spathe*.—Length, overall: About 12 cm. Length, distal open portion: About 8.5 cm; flattened, close to 12.5 cm. Length, proximal closed portion: About 3.5 cm. Width, distal open portion: About 5.4 cm. Width, at constriction: About 2 cm. Width, proximal closed portion: About 2.9 cm. Shape: Roughly ovate to elliptic. Apex: Acute. Base: Tapering to the peduncle. Margin: Entire. Texture, front and rear surfaces: Smooth, glabrous. Color, front surface: Distal open portion: Close to 155D with spots, speckles and coalescing blotches close to 183C to 183D; with development, color becoming closer to 200D. Proximal closed portion: Close to 147C; towards the base, tinged with close to 187A; color does not change with development. Color, rear surface: Distal open portion: Towards the margins, close to 155C with streaks, flecks and spots close to 183C to 183D; center, close to 145C. Proximal closed portion: Close to 147A densely streaked with close to 183A to 183B and 182C.

*Spadix*.—Length: About 9.2 cm. Length, male flower zone: About 6.5 cm. Length, sterile zone: About 1 cm. Length, female flower zone: About 1.7 cm. Diameter, male flower zone: About 1.2 cm. Diameter, sterile flower zone: About 1 cm. Diameter, female flower zone: About 1.1 cm. Shape: Columnar, spindle-shaped. Apex: Bluntly acute. Base: Obtuse. Aspect: Upright. Color, mature, male zone: Close to 11C to 11D. Color, mature, sterile zone: Close to 11C to 11D. Color, mature, female zone: Close to 8C to 8D. Male flowers: Quantity per spadix: About 263. Shape: Obovate. Height: About 3 mm. Diameter: About 3.5 mm. Pollen amount: Abundant. Pollen color: Close to 8D. Female flowers: Quantity per spadix: About 145. Shape: Obovate. Height: About 2.5 mm. Diameter: About 1.5 mm. Stigma color: Close to 4D. Ovary color: Close to 155C.

*Scape*.—Length: About 36 cm. Diameter: About 6 mm. Strength: Sturdy; flexible. Aspect: Mostly erect. Texture: Smooth, glabrous; glaucous. Color: Just below spathe, close to 147B to 147C streaked with close to N170D and 183C to 183D; overall, close to 200A and 200C to 200D streaked with close to N170C.

*Seeds and fruits*.—Seed and fruit development have not been observed on plants of the new *Caladium*.

Disease & pest tolerance: Plants of the new *Caladium* have been observed to have above average tolerance to *Xanthomonas* Leaf Spot and to have average tolerance to *Pythium* Root Rot. Plants of the new *Caladium* have not been observed to have resistance to pests and other pathogens common to *Caladium* plants.

Temperature tolerance: Plants of the new *Caladium* have been observed to be tolerant to temperatures ranging from about 7° C. to about 40° C. and are suitable for USDA Hardiness Zones 8A to 11.

It is claimed:

1. A new and distinct *Caladium* plant named 'Fireworks' as illustrated and described.

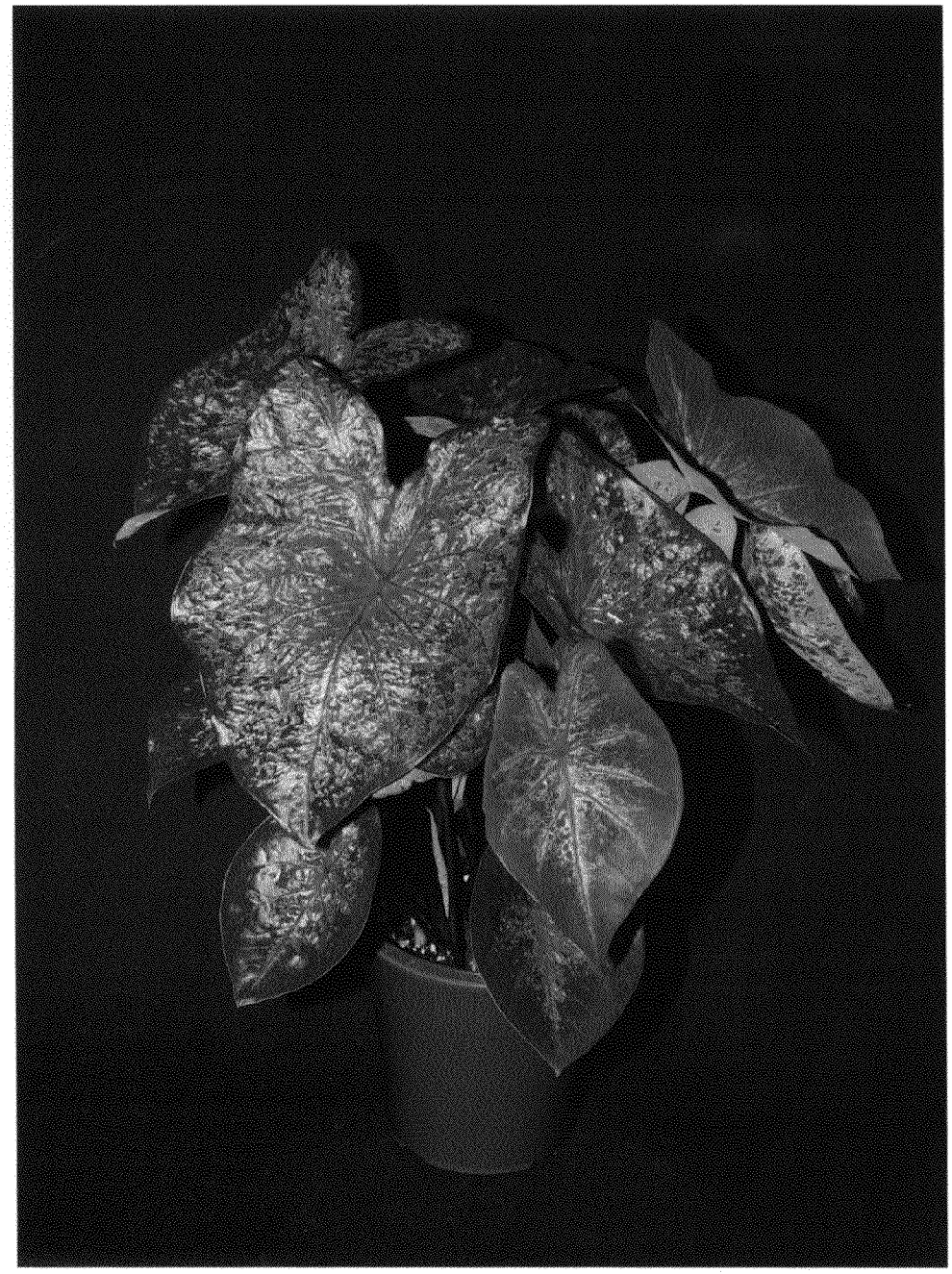

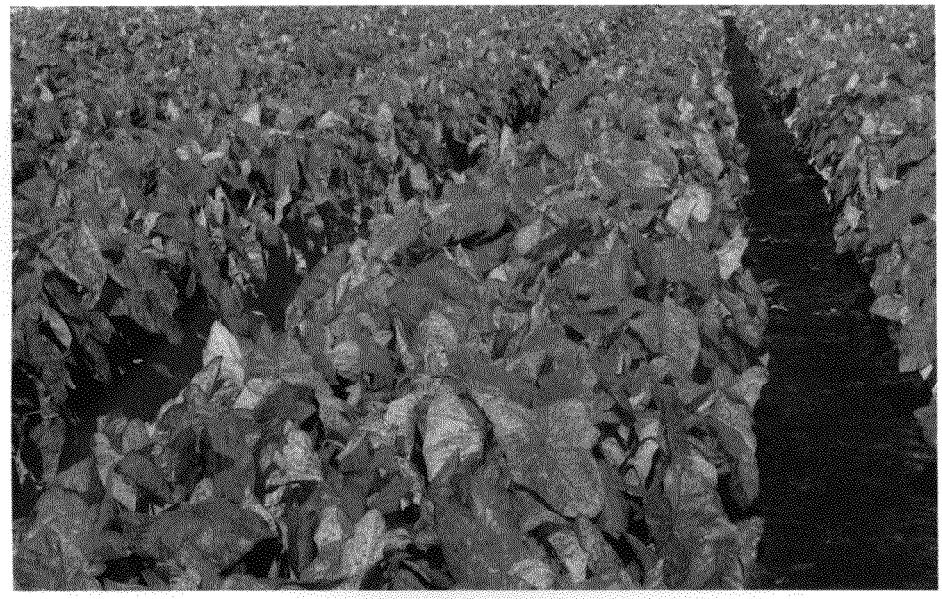
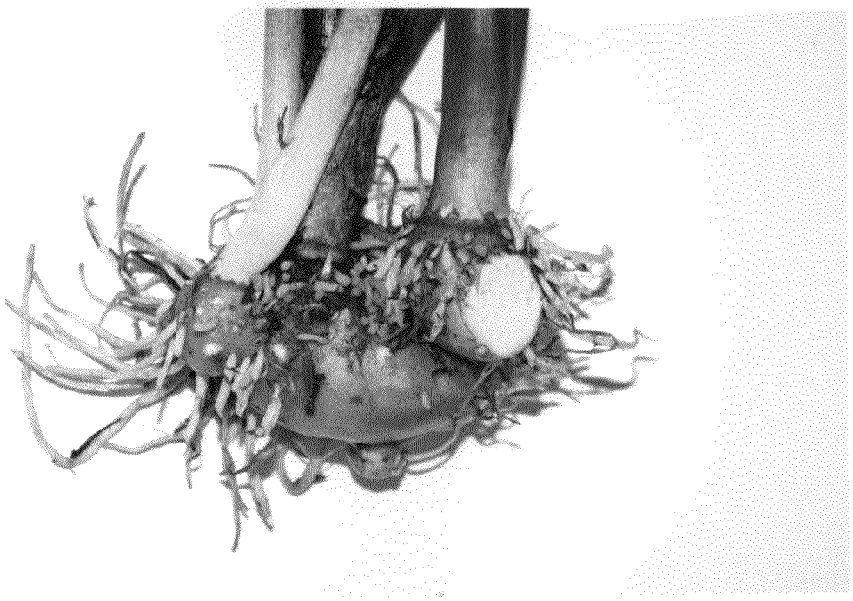

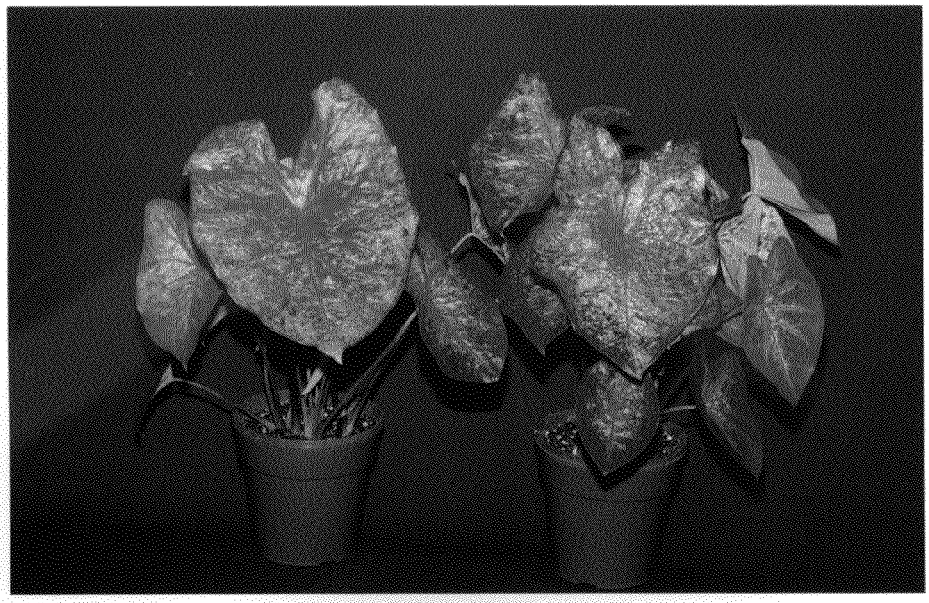
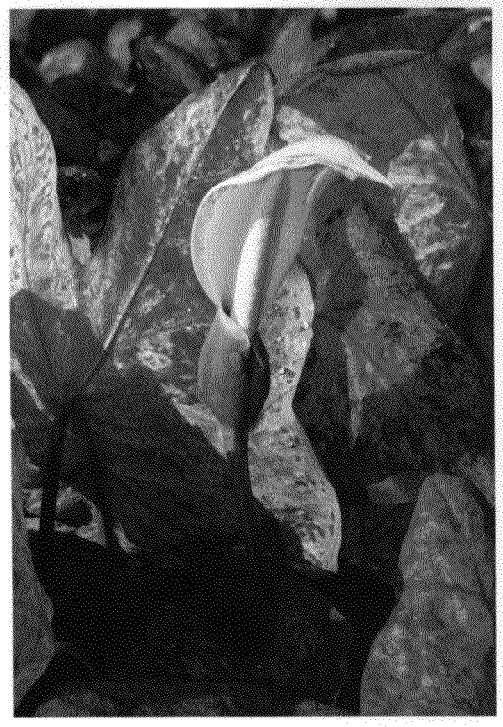

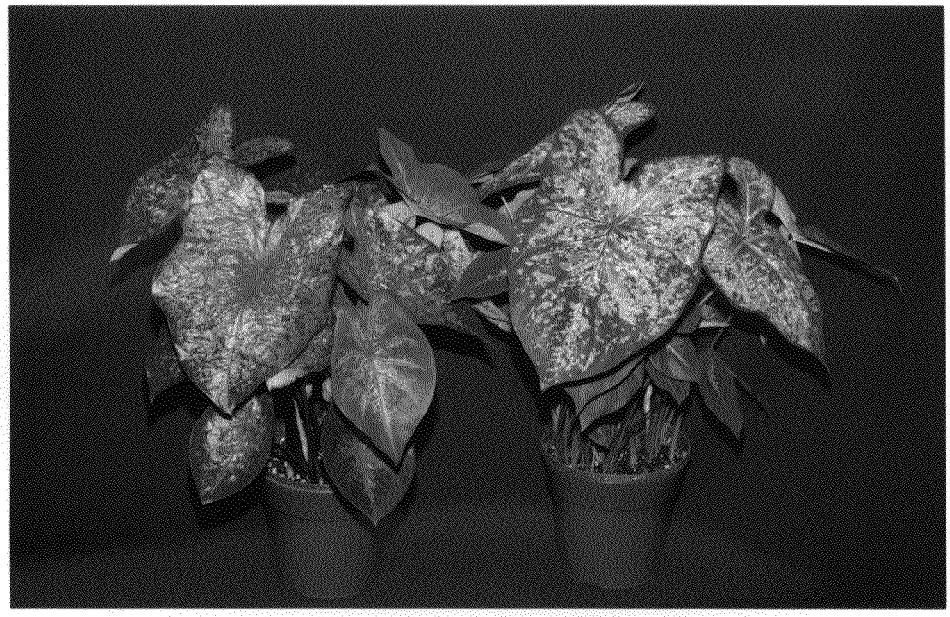
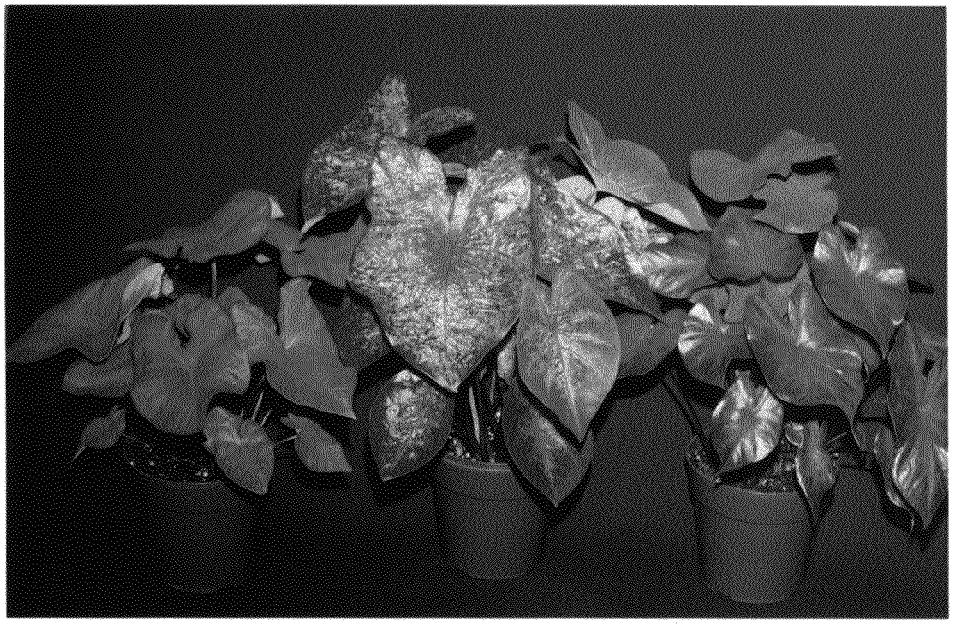

* * * * *